United States Patent [19]

Ali

[11] 4,216,142
[45] Aug. 5, 1980

[54] CHROMOGENIC SUBSTRATES FOR THE PROTEOLYTIC ENZYMES

[75] Inventor: Akhtar Ali, Vernon Hills, Ill.

[73] Assignee: Abbott Laboratories, North Chicago, Ill.

[21] Appl. No.: 970,767

[22] Filed: Dec. 18, 1978

[51] Int. Cl.² .................... C07C 103/52; C12K 1/04
[52] U.S. Cl. .................. 260/112.5 R; 435/13; 435/23
[58] Field of Search ............ 260/112.5 R; 195/99, 195/103.5 R

[56] References Cited

U.S. PATENT DOCUMENTS

| | | | |
|---|---|---|---|
| 4,061,625 | 12/1977 | Ekenstam | 260/112.5 R |
| 4,070,245 | 1/1978 | Svendsen | 260/112.5 R |
| 4,137,225 | 6/1979 | Ekenstam et al. | 260/112.5 R |

Primary Examiner—Donald G. Daus
Assistant Examiner—M. C. Eakin
Attorney, Agent, or Firm—John J. McDonnell; Robert L. Niblack

[57] ABSTRACT

The present invention encompasses a compound of the formula

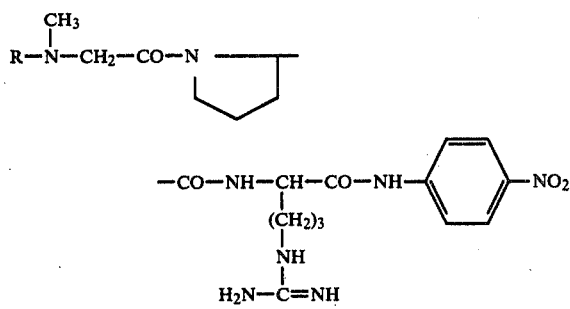

and the biologically acceptable acid addition salts thereof wherein R is hydrogen, tosyl, carbobenzoxy or benzoyl. These compounds are chromogenic substrates for proteolytic enzymes useful in antithrombin III determination.

1 Claim, No Drawings

CHROMOGENIC SUBSTRATES FOR THE PROTEOLYTIC ENZYMES

BACKGROUND OF THE INVENTION

The present invention relates to synthetic reagents or substrates which are used for the quantitative determination of proteolytic enzymes. More particularly, the invention relates to sarcosylproplylarginine-p-nitroanilide derivatives which are useful as reagents for the quantitative determination of proteolytic enzyme which split peptide chains on the carboxyl side of arginine in human and mammal body fluids as well as in vegetable and animal cell extracts and in glandular venoms of cold-blooded animals such as snakes.

U.S. Pat. No. 4,070,245 describes glycylprolylarginine-p-nitroanilide derivatives useful in chromogenic substrates for determining proteolytic enzymes in biological fluids. Compounds of the present invention differ from the prior art in that they terminate with a sarcosine or sarcosine derivative while prior art compounds terminate with glycine or glycine derivatives.

The enzymatic hydrolysis reaction can be represented by the following scheme:

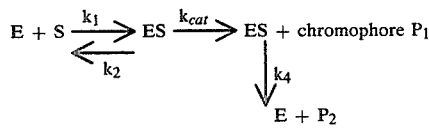

E = enzyme
S = substrate
ES = enzyme-substrate complex
P$_1$ and P$_2$ = products
k$_1$k$_2$k$_{cat}$ and k$_4$ = rate constants
Dissociation constant for ES = k$_2$/k$_1$ = K$_m$(Michaelis constant)
If [S] >> [E] and k$_4$ << k$_{cat}$, the following is true:

$$K_m = \frac{([E] - [ES]) \cdot [S]}{[ES]} \quad (1)$$

The rate constant at which chromophore P$_1$ is formed is: v = k$_{cat}$·[ES]

$$v = \frac{k_{cat} \cdot [E] \cdot [S]}{K_m + [S]} \quad (2)$$

If E is completely bound to S, then [ES] = [E] and $$v = v_{max} = k_{cat} \cdot [E] \quad (3)$$

Lineweaver-Burk equation:

$$\frac{1}{v} = \frac{K_m}{v_{max}} \cdot \frac{1}{[S]} + \frac{1}{v_{max}} \quad (4)$$

As is evident from equation (2) constants K$_m$ and k$_{cat}$ determine the activity of the enzyme substrate for a given enzyme. For determining these constants, the following procedure is followed.

The enzyme and the substrate are mixed in a buffer solution, and the reaction is followed spectrophotometrically for 2 to 30 minutes. The concentration of substrate [S] is varied, whereas the enzyme concentration [E] is kept constant. If the extinction (OD) (= optical density) is plotted in a coordinate system as a function of time, a curve is obtained the tangent of which (difference in extinction per minute, Δ OD/minute, from which the quantity in μmoles of pNA/min(v) can be calculated) at time zero corresponds to the initial course of the hydrolysis. By means of this tangent the initial rate of the hydrolysis can be determined.

If 1/v is plotted against 1/[S], a Lineweaver-Burk diagram is obtained from which v$_{max}$ and K$_m$ can be determined graphically. Thus K$_m$ and k$_{cat}$ can be determined.

SUMMARY OF THE INVENTION

The present invention encompasses chromogenic substrates which are sarcosylprolylarginine-p-nitroanilides and carbobenzoxy, tosyl, benzoyl derivatives thereof and their biologically acceptable acid addition salts. These compounds are useful as chromogenic substrates for proteolytic enzymes and permit the determination of clinically useful substances such as antithrombin III.

DETAILED DESCRIPTION OF THE INVENTION

Chromogenic substrates of the present invention are prepared by the following scheme:

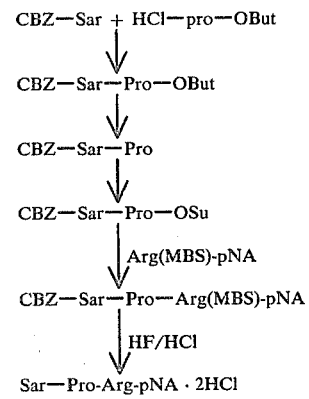

CBZ = carbobenzoxy
Sar = sarcosine
Pro = proline
HF = hydrofluoric acid
OSu = succinimidyl ester
MBS = methoxybenzenesulfonyl
pNA = p-nitroanilide
OBut = tertiary butyl ester Sar-Pro-Arg-pNA can be protonized with mineral acids such as HCl, HBr, H$_2$SO$_4$ or H$_3$PO$_4$ or organic acids such as formic, acetic, oxalic and tartaric to provide biologically compatible acid addition salts.

CBZ can be replaced by other groups such as tosyl and benzoyl. Those skilled in the peptide synthetic arts will recognize a wide variety of synthetic approaches to tripeptides of this sort.

Using the kinetic analysis set out in the background section of the invention, Sar-Pro-Arg-pNA.2HCl, 0.1 M in 0.17 M Tris buffer, pH 7.4 and human thrombin, 0.63 mg/ml, reacted at 37° C. and monitored at 405 nm provides k$_{cat}$ = 158 sec$^{-1}$ and K$_m$ = 9.2 × 10$^{-4}$ M.

Clinically, the chromogenic substrate is used to measure antithrombin III.

Antithrombin III (AT III) is the major component of the anticoagulation system. It inhibits a variety of serine proteases by forming a 1:1 complex via serine, the active center of such enzymes. The presence of heparin increases the rate of reaction of AT III with such proteases approximately 100 fold, making AT III the only plasma component involved in this rapid inhibition reaction.

The chemistry of the AT III is described in the following equations:

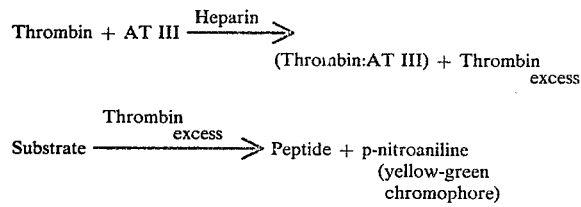

Since the presence of heparin potentiates the activity of AT III, it is possible to delineate the inhibition due to AT III from that of other plasma proteins which can also inhibit thrombin. Thus, one measures total AT III activity as an entity distinct from the "progressive antithrombin activity" which is measured in the absence of heparin. As a result, one can clearly identify a defect in the anticoagulation system as one associated with AT III rather than other protein inhibiting mechanism.

This test relies on the fact that human AT III in a specimen inhibits human α-thrombin in a 1:1 molar ratio. Excess thrombin is free to hydrolyse a colorless chromogenic substrate. When this substrate is cleaved, it releases p-nitroaniline, a chromophore which causes a dramatic shift in the absorbance spectrum shown by the development of a yellow-green color. This cleavage of the substrate is analogous to the cleavage of the arginyl-glycine bond in fibrinogen which results in the formation of fibrin. By monitoring the color development of the reaction mixture, one can follow the course of the turnover of substrate by thrombin. Since the amount of AT III and the amount of color produced are inversely proportional, the level of AT III can readily be determined.

In order to provide a simple, rapid and reproducible assessment of AT III activity, three standards of highly purified AT III activity enable one to plot a standard curve from which unknown AT III levels are determined.

Preferably, 0.8 mM sarcosyl-L-prolyl arginine-p-nitroanilide in mannitol containing hexadimetrine bromide, 0.7 mg/ml as heparin neutralizer, is used as a chromogenic reagent containing substrate. Generally, the test is made in conjunction standards containing 50, 100, and 125% the normal amount of antithrombin III. The p-nitroaniline released is monitored at 405 nm.

Compounds of the present invention can be used in the tests described in U.S. Pat. No. 4,070,245. The hereinafter set forth examples are intended to illustrate the present invention and not limit it in scope or spirit.

EXAMPLE I

Preparation of (L-Arg-(MBS)-pNA.HBr)

$N^\alpha$-carbobenzoxy-ω-methoxybenzenesulfonyl-L-arginine (23.0 g) is dissolved in 100 ml of hexamethylphosphoramide and to this solution is added 6.7 ml of triethylamine and 15.8 g of p-nitrophenyl isocyanate. The reaction mixture is stirred at room temperature overnight and then poured into 130 ml of 5% sodium bicarbonate. The resulting precipitate is filtered and washed with (2×400 ml) of 5% sodium bicarbonate, (1×300 ml) of water, (3×300 ml) of 1N hydrochloric acid and (2×200 ml) of water. The filter cake is dried on the funnel by vacuum suction and then extracted with boiling methanol (3×300 ml). The combined methanol extracts is evaporated under reduced pressure at 35° C. The semi-solid residue is purified further by a silica gel column using chloroform:acetic acid:methanol (94:5:1) as eluent. This provides $N^\alpha$-carbobenzoxy-ω-methoxybenzenesulfonyl-L-arginine p-nitroanilide (CBZ-L-Arg(MBS)-pNA). 6.0 g of this material is dissolved in 30% hydrobromic acid in acetic acid. The reaction mixture is kept at room temperature for 45 minutes and then poured into 400 ml of dry ether. The precipitated salt is filtered and washed with (2×100 ml) of dry ether to provide ω-methoxybenzenesulfonyl-L-arginine-p-nitroanilide.hydrobromide (L-Arg(MBS)-pNA-HBr).

Preparation of carbobenzoxy-sarcosyl-L-proline-succinimidyl ester: 4.5 g of CBZ-sarcosine is dissolved in 100 ml tetrahydrofuran and 2.4 ml of n-methylmorpholine is added. The reaction mixture is cooled to −10° C. and stirred while 2.6 ml of isobutylchloroformate is added. After 5 minutes of additional stirring at −10° C. 4.15 g L-proline-t-butylester hydrochloride in 100 ml of tetrahydrofuran and 3.0 ml of n-methylmorpholine are added to the reaction mixture. The reaction mixture is stirred overnight and slowly warmed to room temperature. The solvent is evaporated under reduced pressure at 30° C. and the residue is dissolved in 600 ml ethylacetate. The ethylacetate layer is washed with (3×150 ml), 1N sodium hydroxide, water (1×200 ml) 10% citric acid (3×150 ml), and water (3×150 ml). The organic layer is dried over anhydrous magnesium sulfate, filtered and evaporated under reduced pressure to provide carbobenzoxysarcosyl-proline-t-butyl ester (CBZ-Sar-L-Pro-O-t-But). 6.5 g of this material is dissolved in 15 ml of methylene chloride and 25 ml of trifluoroacetic acid is then added. The reaction mixture is kept at room temperature for 45 minutes and then the solvent is evaporated under reduced pressure at 30° C. The residue is triturated with hexane (3×50 ml) and the hexane removed by decantation. The residue is evaporated from (2×50 ml) of benzene to provide an oily residue which is carbobenzoxysarcosyl-L-proline (CBZ-Sar-L-Pro). 5.4 g of this material and 3.45 g of N-hydroxysuccinimide are dissolved in 100 ml of tetrahydrofuran and cooled to 0° C. To this cooled reaction mixture is added 4.12 g of dicyclohexylcarbodiimide. The reaction mixture is stirred overnight at 4° C. and the solvent is evaporated under reduced pressure. The residue is dissolved in 400 ml of ethylacetate and the dicyclohexyl urea is filtered off. The filtrate is washed with 1N-hydrochloric acid (3×100 ml), water (1×100 ml), saturated sodium bicarbonate solution (2×100 ml) and water (2×100 ml). The organic layer is dried over anhydrous magnesium sulfate, filtered and the solvent is evaporated under reduced pressure to provide carbobenzoxy-sarcosyl-L-proline-succinimidyl ester.

Preparation of Sar-Pro-Arg-pNA.2HCl: To 1.8 g of L-Arg(MBS)-pNA dissolved in 10 ml of dimethylformamide and neutralized with n-methylmorpholine is added 2.1 g of CBZ-Sar-Pro-Osu. The mixture is stirred overnight. The solvent is evaporated under reduced pressure at 35° C. and the residue taken up in 500 ml of ethylacetate. The organic layer is washed with 1N hydrochloric acid, (3×100 ml), water (1×100 ml), 1N sodium hydroxide (3×100 ml) and water (2×100 ml). The ethyl acetate layer is dried over anhydrous magnesium sulfate, filtered and the solvent evaporated. The resulting crude solid is purified on a silica gel column using chloroform: methanol (98:2) as a solvent. This procedure provides carbobenzoxy-sarcosyl-L-prolyl-ω-p-methoxybenzenesulfonyl-L-arginine-p-nitroanilide.

750 mg of this material is dissolved in liquid hydrofluoric acid and the hydrofluoric acid is allowed to evaporate and the residue is partitioned between 100 ml of ether and 30 ml of 1N of 1N-hydrochloric acid. The aqueous layer is separated and lyophilized. The crude product is purified by chromatography ong a G-25 Sephadex using 30% acetic acid as eluent to provide sarcosylprolylarginine-p-nitrophenylanilide hydrochloride having the formula Sar-Pro-Arg-pNA.2HCl.

EXAMPLE II

Sarcosylprolylarginine-p-nitrophenylanilide (4 mM) is reacted with an equivalent of p-toluenesulfonyl-chloride (tosyl chloride) in 25 ml of dimethyl formamide containing an equivalent of triethyl amine. The reaction mixture was worked up as in Example I to provide $N^\alpha$-tos-Gly-Pro-Arg-pNA.HCl. The procedure is substantially the same as that described in U.S. Pat. No. 4,070,245.

EXAMPLE III

Following the procedure in Example II, substituting benzoylchloride for tosylchloride provides $N^\alpha$-benzoyl-sarcosyl-prolylarginine-p-nitroanilide.hydrochloride.

What is claimed is:
1. A compound which is

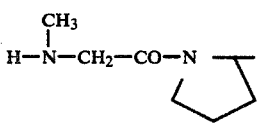
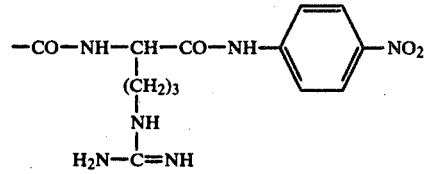

and the hydrochloride salt thereof.

* * * * *